US007858349B2

(12) United States Patent
Stewart et al.

(10) Patent No.: US 7,858,349 B2
(45) Date of Patent: Dec. 28, 2010

(54) ANTI-CANCER COMPOUNDS

(75) Inventors: John M. Stewart, Denver, CO (US); Daniel C. F. Chan, Denver, CO (US); Lajos Gera, Denver, CO (US); Paul A. Bunn, Jr., Evergreen, CO (US)

(73) Assignee: The Regents of the University of Colorado, Denver, CO (US)

( * ) Notice: Subject to any disclaimer, the term of this patent is extended or adjusted under 35 U.S.C. 154(b) by 165 days.

(21) Appl. No.: 12/212,604

(22) Filed: Sep. 17, 2008

(65) Prior Publication Data

US 2009/0088454 A1  Apr. 2, 2009

Related U.S. Application Data

(63) Continuation of application No. 11/304,269, filed on Dec. 14, 2005, now Pat. No. 7,427,496, which is a continuation-in-part of application No. 10/035,662, filed on Dec. 28, 2001, now Pat. No. 7,071,168, which is a continuation of application No. 09/378,019, filed on Aug. 19, 1999, now Pat. No. 6,388,054.

(60) Provisional application No. 60/141,169, filed on Jun. 25, 1999.

(51) Int. Cl.
 *C12P 13/04* (2006.01)
 *A61K 38/00* (2006.01)
 *A61K 49/00* (2006.01)

(52) U.S. Cl. .................. 435/106; 435/117; 435/7.1; 424/9.1; 562/433; 530/300; 530/314; 530/333; 530/402

(58) Field of Classification Search .............. 435/106, 435/117, 7.1; 424/9.1; 562/433; 530/300, 530/314, 333, 402
See application file for complete search history.

(56) References Cited

U.S. PATENT DOCUMENTS

| 3,235,594 | A | 2/1966 | Levi et al. |
|---|---|---|---|
| 4,904,680 | A | 2/1990 | Matsui et al. |
| 5,635,593 | A | 6/1997 | Cheronis et al. |
| 5,849,863 | A | 12/1998 | Stewart |
| 6,388,054 | B1 | 5/2002 | Stewart et al. |
| 7,071,168 | B2 | 7/2006 | Stewart et al. |
| 7,427,496 | B2 | 9/2008 | Stewart et al. |

FOREIGN PATENT DOCUMENTS

WO   WO 97/09347   3/1997

OTHER PUBLICATIONS

D. Chan, et al., "Novel bradykinin antagonist dimers for the treatment of human lung cancers," Immunopharmacology, vol. 33, 1996, pp. 201-204.

L. Gera, et al., "New Bradykinin Antagonists Having High Potency at Both B1 and B2 Receptors," Peptides: Chemistry, Structure and Biology, Mayflower Scientific Ltd., 1996, pp. 348-349.

Stewart et al., Can. J. Physiol. Pharmacol. 75:719-724, 1997.

International Search Report for International (PCT) Patent Application No. PCT/US99/19381, mailed Feb. 10, 2000.

Written Opinion for International (PCT) Patent Application No. PCT/US99/19381, mailed Oct. 5, 2000.

International Preliminary Examination Report for International (PCT) Patent Application No. PCT/US99/19381, mailed Apr. 24, 2001.

Bawolak MT, Gera L, Morissette G, Stewart JM, Marceau F. B-9972 (D-Arg-[Hyp(3), Igl(5),Oic(7), Igl(8)]-bradykinin) is an inactivation-resistant agonist of the bradykinin B-2 receptor derived from the peptide antagonist B-9430 (D-Arg-[Hyp(3), Igl(5), D-Igl(7), Oic(8)]-bradykinin): Pharmacologic profile and effective induction of receptor degradation. Journal of Pharmacology and Experimental Therapeutics 323 (2): 534-546, 2007.

Morissette G, Houle S, Gera L, Stewart JM, Marceau F. Antagonist, partial agonist and antiproliferative actions of B-9870 (CU201) as a function of the expression and density of the bradykinin B-1 and B-2 receptors. British Journal of Pharmacology 150 (3): 369-379 Feb. 2007.

Larrivee JF, Gera L, Houle S, Bouthillier J, Bachvarov DR, Stewart JM, Marceau F. Non-competitive pharmacological antagonism at the rabbit B-1 receptor. British Journal of Pharmacology, 131 (5): 885-892,2000.

Gera L, Fortin JP, Adam A, Stewart JM, Marceau F. Discovery of a dual-function peptide that combines aminopeptidase N inhibition and kinin B-1 receptor antagonism. Journal of Pharmacology and Experimental Therapeutics, 317 (1): 300-308, 2006.

Inamura et al., "Characterization of FR173657, a novel, non-peptide BK2 antagonist, in vitro and in vivo", Can. J. Physiol. Pharmacol. 75, 622-628 (1997).

L. Gera at al., A new class of potent bradykinin antagonist dimers. Immunopharmacology (1996), 33(1-3), 178-82.

L. Gera and JM. Stewart, A new class of bradykinin antagonists containing indanylglycine. Immunopharmacology (1996), 33(1-3), 174-77.

Griesbacher et al. "The nonpeptide B2 receptor antagonist FR173657: inhibition of effects of bradykinin related to its role in nociception" British Journal of Pharmacology (1998) 124, 1328-1334.

*Primary Examiner*—Chih-Min Kam
(74) *Attorney, Agent, or Firm*—Sheridan Ross, P.C.

(57) ABSTRACT

The invention provides bradykinin antagonists and pharmaceutically acceptable salts thereof having anti-cancer activity. These anti-cancer compounds are particularly useful for inhibiting the growth of lung and prostate cancers.

5 Claims, No Drawings

US 7,858,349 B2

ANTI-CANCER COMPOUNDS

CROSS REFERENCE TO RELATED APPLICATION

This application is a continuation of U.S. patent application Ser. No. 11/304,269, filed Dec. 14, 2005, now U.S. Pat. No. 7,427,496, which is a continuation in part of U.S. patent application Ser. No. 10/035,662, filed Dec. 28, 2001, now U.S. Pat. No. 7,071,168, which is a continuation of U.S. patent application Ser. No. 09/378,019, filed Aug. 19, 1999, now U.S. Pat. No. 6,388,054, which claims priority under 35 U.S.C. §119(e) to U.S. Provisional Patent Application No. 60/141,169 filed Jun. 25, 1999. These priority documents are incorporated herein in their entirety by this reference.

GOVERNMENT INTEREST

This invention was made with Government support under grant numbers HL-26284 awarded by the National Heart, Lung and Blood institute and CA-78154 awarded by the National Cancer Institute of the U.S. National Institutes of Health. The Government has certain rights in this invention.

FIELD OF THE INVENTION

The invention relates to anti-cancer compounds and methods of making and using these compounds.

BACKGROUND OF THE INVENTION

Many lung and prostate cancers, of which small cell lung cancer (SCLC) is a prime example, have a neuroendocrine phenotype, and their growth is stimulated by neuropeptides. Antagonists of several peptides (e.g. bradykinin, substance P, bombesin) have been used in experimental treatment of models of SCLC in animals. Among the most potent of the peptides examined thus far, crosslinked dimers of bradykinin antagonist peptides have been efficacious both in vitro and in vivo against strains of SCLC and other tumors (Chan et al., *Immunopharmacology* 33: 201-204, 1996; Stewart et al., *Can. J. Physiol. Pharmacol.* 75: 719-724, 1997; Stewart et al., U.S. Pat. No. 5,849,863). Prostate cancers show a similar neuroendocrine phenotype and are susceptible to these neuropeptide antagonists.

Bradykinin (BK: Arg-Pro-Pro-Gly-Phe-Ser-Pro-Phe-Arg (SEQ ID NO: 1)) is an important growth factor for many types of cancers. Many cancers express receptors for BK and overproduce BK to stimulate their growth. In addition to direct stimulation of cancer growth, BK stimulates angiogenesis in solid tumors by stimulating release of vascular endothelial growth factor (VEGF) and facilitates tumor spreading and invasion by stimulating release of matrix metalloproteases (MMPs). Thus, antagonists of BK have three potential tumor-inhibiting activities.

The first BK antagonists developed were peptides which did not show any anti-cancer activity. Thereafter, several non-peptide BK antagonists were reported from several laboratories (Inamura et al., *Can. J. Physiol. Pharmacol.* 75: 622-628, 1997). The present inventors also discovered a group of acylated amino acid amides having BK antagonist activity that are also potent anti-cancer agents (see U.S. Pat. No. 6,388,054). Following the discovery that certain dimerized bradykinin antagonist peptides are cytotoxic for cancer cells and inhibit tumor growth, interest grew in finding smaller, non-peptide BK antagonists with similar anti-cancer efficacy but lower cost of synthesis as well as the possibility non-parenteral routes of administration.

SUMMARY OF THE INVENTION

The present invention provides anti-cancer agents comprised of a range of novel acyl amino acid amide derivatives having BK antagonist activity and having the ability to inhibit growth of small cell lung cancer (SCLC), non-small cell lung cancer (NSCLC) and prostate cancer (PC) cells in standard in vitro tests as well as to inhibit growth of these cancers in vivo in tumors implanted subcutaneously in athymic nude mice. The anti-cancer agents in this application are derivatives of compound M570, which has the chemical structure: Pentafluorocinnamoyl-O-(2,6-dichlorobenzyl)tyrosine-4-amino-2,2,6,6-tetramethylpiperidine (Abbreviated F5C-OC2Y-Atmp).

M570 was disclosed in U.S. Pat. No. 6,388,054, and is a potent inhibitor of SCLC, NSCLC and PC growth, both in vitro and in vivo. The compounds of the present invention were obtained by replacement of one or two of the three functional groups in M570 to produce more potent anti-cancer compounds that are advantageously more soluble and may preferably be administered orally.

The present invention also provides methods of inhibiting cancer growth by administering to a subject afflicted with cancer a therapeutically effective amount of one or more of the compounds of the present invention.

DETAILED DESCRIPTION OF THE INVENTION

Non-peptide compounds have recently been described as antagonists for a variety of peptide hormones, including bradykinin. Such peptide mimetics are pharmaceutically desirable, as they are more likely to be orally available and are less likely to be susceptible to enzymatic degradation. Although there are few guidelines to direct a search for such compounds, the present inventors synthesized various molecules containing the presumed requisite hydrophobic and basic groups and examined these compounds for anti-bradykinin and anti-cancer activity. Several potent anti-cancer compounds were found in this search.

Anti-cancer activity was determined on cultured human cancer cell lines using the standard tetrazolium (MTT) assay and in human cancers implanted subcutaneously in athymic nude mice. Potent compounds were found to stimulate apoptosis in SCLC cells. They inhibited implanted tumors by inhibiting growth directly, by inhibiting neovascularization and by inhibiting matrix metalloproteases, which are important for tumor extension and migration.

The anti-cancer compounds of the present invention have the chemical formula:

$$A\text{-}B\text{---}R \qquad \text{(Formula I)}$$

wherein,

A is an acylating group, and preferably a hydrophobic acylating group, or an anti-inflammatory substituent;

B is an amino acid or substituted amino acid; and,

R is a substituted amide, preferably having additional polar character.

Abbreviations of the chemical entities that compose the anti-cancer compounds of the present invention that are used in this disclosure are listed in Table 1.

With reference to Table 1, the group A acylating groups may be chosen from: Aaa, Aba, Aca, Acrc, Aic, Amts, 6Ani, Aq2c, Arac, Aspr, Atfb, 4Atfb, B6, B6P, Baaa, Bbz, Bcin, Bcpa, Bcpoa, Biot, Bipa, 4 Bpc, Bphs, tBua, Bzac, Chbu, Chc, CHFB, Chl, Chpa, 2Cln, Cmioc, Cpcpc, Dbhc, Dca, Dcla, tDecl, Dfc, Dhq, Dmc, Dmo, 22Dp, Esul, 2-Fa, 3-Fa, F5b, F5bs, F5bz, F3c, F5c, Fcin, αFcn, Fmoc, F5pa, Fmpi, F5po, F5pt, Gbz, Hcn, Hmqc, Hor, 2Hyb, 3Iac, 3Ibu, 2Ina, Indo, Inp, Ktlc, Ktpf, Mca, αMcn, Mcoa, 34Mdc, MTPA, 1Nac, 1Nala, Nap, Napr, Nba, Octe, Otac, Pac, Pas, Pcin, Pcn, Pcnl, βPhc, 3Php, 5Phv, Pic, Piva, Ppr, Ptmb, αPtpa, Pya, Pyrc, Pyz, 13cR, Ret, Rio, Saa, Sab, cSdc, Sibu, cSsa, tβSts, Taa, Tchc, Tcpa, Tf2c, 4Tfmb, Thia, Th2n, Tic, Tmb, 4Tmbs, Tmbz, Tmcc, or ZPcn.

Group A anti-inflammatory substitutents may include indomethacin (Indo), aspirin (Aspr), naproxen (Napr), diclofenac (Dfc), ketoprofen (Ktpf) or ketorolac (Ktlc). Because solid tumors are surrounded by a zone of inflammation, anti-cancer analogs having the F5C moiety of M570 replaced by non-steroidal anti-inflammatory drugs (NSAIDS) were synthesized. Although standard NSAIDS are typically administered as free acids, esters or amides of these are also effective. Some of these anti-inflammatory compounds are potent anti-cancer agents in their own right. Combined in the structure of the anti-cancer bradykinin antagonists of the present invention, the resulting compounds are particularly effective anti-cancer agents.

Group B amino acids may be chosen from: Bip, Ddip, F5F, F3MF, hPhe, MC2Y, Nal, NMF, OBPY, OBrZY, OC2Y, OCIY, Pal, PBF, PCNF, PFF, PIF, PNF, Tic, or Tyr(Bzl).

Group R amide groups may be chosen from: Abzp, Aem, Alp, Ambi, Apia, Apyr, AquR, Atmp, BapR, BapS, Bdbh, Bhp, Btmb, Cbp, Chmp, tCip, 4Clbp, Cpp, Cypp, Daep, Dasd, Dcpp, cDmap, cDmbp, cDmm, Dmmp, Dmpz, Dpic, Fbhp, 4Fbp, Fpmp, Fpdh, Matp, 4 Mbp, Mpz, Ocp, Pep, Pipe, Pipp, Pipz, Pmpz, Ppp, Pypz, 3Qum, or Tmbp.

TABLE 1

Abbreviations for Chemical Groups Used to Synthesize the Anti-Cancer Compounds of the Present Invention Aaa = 1-Adamantaneacetyl
Aba = 2-cis-4-trans-Abscisic acid
Abzp = 4-Amino-1-benzylpiperidine
Aca = 1-Adamantanecarboxyl
Acrc = Acridine-9-carboxyl
Aem = 4-(2-Aminoethyl)-morpholine
Aic = 2-Aminoindane-2-carboxylic acid
Alp = 1-Allylpiperazine
Ambi = 2-(Aminomethyl)benzimidazole
Amp = 1-(3-Aminopropyl)-4-methylpiperazine
Amts = 2-Acetamido-4-methyl-5-thiazolesulfonyl
6Ani = 6-Aminonicotinoyl
Apia = 1-(3-Aminopropyl)imidazole
Apyr = 3-Amino-pyrrolidine
Aq2c = Anthraquinone-2-carboxyl
AquR = (R)-(+)-3-Aminoquinuclidine
Arac = Arachidonyl
Aspr = O-Acetylsalicyl: 2-acetoxybenzoyl
Atfb = 3-Amino-2,5,6-trifluorobenzoyl
4Atfb = 4-Amino-2,3,5,6-tetrafluorobenzoyl
Atmp = 4-Amino-2,2,6,6-tetramethylpiperidine
AtmpO = 4-Amino-2,2,6,6-tetramethylpiperidinyloxy
B6 = 3-Hydroxy-5-(hydroxymethyl)-2-methyl-4-pyridylmethyl (Vitamin B6, Pyridoxamine)
B6P = 3-Hydroxy-5-(hydroxymethyl)-2-methyl-4-pyridylmethyl-5-phosphate
Baaa = 2,2-Bis(acrylamido)acetyl
BapR = (R)-(−)-1-Benzyl-3-aminopyrrolidine
BapS = (S)-(+)-1-Benzyl-3-aminopyrrolidine
Bbz = 4-Boronobenzoyl
Bcin = 4-Boronocinnamoyl
Bcpa = bis(4-Chlorophenyl)acetyl
Bcpoa = bis(4-Chlorophenoxy)acetyl
Bdbh = (1S,4S)-(+)-2-Benzyl-2,5-

TABLE 1-continued

Abbreviations for Chemical Groups Used to Synthesize the Anti-Cancer Compounds of the Present Invention diazabicyclo[2.2.1]heptane
Bhp = 1-Benzylhomopiperazine
Biot = Biotinyl
Bip = β-(4-Biphenylyl)alanine
Bipa = 4-Biphenylacetyl
4Bpc = 4-Biphenylcarboxyl
Bphs = 4-Biphenylsulphonyl
Btmb = 3,5-Bis(trifluoromethyl)benzylamine
tBua = tert-Butylacetyl
Bzac = 3-Benzoylacryloyl
Cbp = 1-(4-Chlorobenzhydrylpiperazine)
2Ccn = 2-Chlorocinnamoyl
Chbu = 2-Cyclohexylbutyryl
Chc = α-Cyano-4-hydroxycinnamoyl
CHFB = 4-Carboxy-hexafluorobutyryl
Chl = Chlorambucil: 4-[p-(bis[2-Chloroethyl]amino)-phenyl]butyryl
Chmp = 1-Cyclohexylmethylpiperazine
Chpa = α-Cyclohexylphenylacetyl
tCip = trans-1-Cinnamylpiperazine
4-Clbp = 1-(4-Chlorobenzyl)piperazine
2Cln = 2-Chloronicotinoyl
Cmioc = 3-(2-Chlorophenyl)-5-methylisoxazole-4-carbonyl
Cpcpc = 1-(4-Chlorophenyl)-1-cyclopropanecarboxyl
Cpp = 1-(4-Chlorophenyl)piperazine
Cypp = 1-(4-Cyanophenyl)piperazine
Daep = 1-(2-(Diallylamino)ethyl)piperazine
Dasd = 1,4-Dioxa-8-azaspiro[4.5]decane
Dbhc = 3,6-Di-tert-butyl-4-hydroxycinnamoyl
Dca = Dicyclohexylacetyl
Dcla = Dichloroacetyl
Dcpp = 1-(2,3-dichlorophenyl)piperazine
tDecl = trans-4-(Diethylamino)cinnamyl
Dfc = Diclofenac: 2-[(2,6-Dichlorophenyl)amino]phenylacetyl
Dhq = 2,3-Dehydroquinuclidine-3-carboxyl
Dip = 3,3-Diphenylalanine
cDmap = cis-2,6-Dimethyl-1-allyl-piperazine
cDmbp = cis-2,6-Dimethyl-1-benzylpiperazine
Dmc = Dimethoxycinnamoyl
CDmm = cis-2,6-Dimethylmorpholine
Dmmp = cis-2,6-Dimethyl-1-(methoxycarbonylmethyl)piperazine
Dmo = 3,7-Dimethyl-6-octenoyl: R-+-Citronellyl
Dmpz = 2,6-Dimethylpiperazine
22Dp = 2,2-Diphenylpropionyl
Dpic = Di-(2-picoyl)amine
Esul = Exisulindacyl: (Z)-5-Fluoro-2-methyl-[[4-(methylsulfonyl)phenyl]methylene]-1H-indene-3-acetyl; (cis)
2-Fa = 2-Furanacryloyl
3-Fa = trans-3-Furanacryloyl
F5b = 2,3,4,5,6-Pentafluorobenzyl
Fbhp = 1-(4-Fluorobenzyl)homopiperazine
4-Fbp = 1-(4-Fluorobenzyl)piperazine
F5bs = Pentafluorobenzenesulfonyl
F5bz = Pentafluorobenzoyl
F3c = 2,3,5-Trifluorocinnamoyl
F5c = 2,3,4,5,6-Pentafluorocinnamoyl
Fcin = 4-Formylcinnamoyl
αFcn = αFluorocinnamoyl
F5F = Pentafluorophenylalanine
F3MF = 4-Trifluoromethylphenylalanine
Fmoc = 9-Fluorenylmethoxycarbonyl
F5pa = 2,3,4,5,6-Pentafluorophenylacetyl
Fpmp = 1-bis(4-Fluorophenyl)methylpiperazine
Fmpi = (Z)-5-Fluoro-2-methyl-(4-pyridylidene)-3-indenylacetyl
F5po = 2,3,4,5,6-Pentafluorophenoxyacetyl
F5Pt = Pentafluorophenylthiocarbamyl
Fpdh = (1S,4S)-(−)-2-(4-Fluorophenyl)-2,5-diazabicyclo[2.2.1]heptane
Gbz = 4-Guanidinobenzoyl
Gun = Guanidyl
Hcn = 9-(N-Hydroxycarbamoyl)-nonanoyl
Hmqc = 3-Hydroxy-2-methyl-4-quinolinecarboxyl TABLE 1-continued Abbreviations for Chemical Groups Used to Synthesize
the Anti-Cancer Compounds of the Present Invention Hor = (S)-(+)-Hydroorotic acid
HPhe = Homo-phenylalanine
2Hyb = 2-Hydroxybenzoyl
3Iac = 3-β-Indoleacryloyl
3Ibu = Indole-3-butyryl
Igl = α-2-Indanylglycine
2Ina = 2-Indanylacetyl
Indo = Indomethacin: 1-[p-Chlorobenzoyl]-5-methoxy-
2-methylindole-3acetyl
Inp = Isonipecotic acid: hexahydroisonicotinic
Isoquinolineacetyl
Ktlc = Ketorolac: (+)5-benzoyl-2,3dihydro-1H-
pyrrolizine-1-carboxyl: Toradol
Ktpf = Ketoprofen: 2-(3-benzoylphenyl)propionyl
Matp = 4-(Methylamino)-2,2,6,6-tetramethylpiperidine
4-Mbp = 1-(4-Methylbenzyl)piperazine
Mca = 2-Methylcinnamoyl
αMcn = α-Methylcinnamoyl
Mcoa = 7-Methoxycoumarin-4-acetyl
MC2Y = N-Methyl-O-2,6-dichlorobenzyl-tyrosine
34Mdc = 3,4-(methylenedioxy)cinnamoyl
Mpz = 1-Methylpiperazine
MTPA = α-Methoxy-α-trifluoromethylphenylacetyl
1Nac = 3-(1-Naphthyl)acryloyl
Nal = β-Naphthylalanine
1Nala = Naphthylacetyl
Nap = Naphthoyl
Napr = Naproxen: 6-Methoxy-α-methyl-2-
Naphthaleneacetyl
Nba = Norbornane-2-acetyl
Nif = Niflumic acid, 2-(3-
[Trifluoromethyl]aniline)nicotinic acid
NMF = N-Methylphenylalanine
OBPY = O-Benzyl-phosphotyrosine
OBrZY = (O-2-Bromo-Cbz)-tyrosine
OCIY = O-2,6-Dichlorobenzyl-3,5-diiodo-tyrosine
OC2Y = O-2,6-dichlorobenzyl tyrosine
Ocp = 1-Octylpiperazine
Octe = 2-Octenoyl
Otac = (−)-2-Oxo-4-thiazolidinecarboxyl
Pac = 4-Aminocinnamic acid
Pal = β-(3-Pyridyl)alanine
Pas = p-Aminosalicyloyl
PBF = p-Bromophenylalanine
Pcin = 4-Phenylcinnamoyl
Pcn = α-Phenylcinnamoyl
PCNF = p-Cyano-L-phenylalanine
Pcnl = β-Phenylcinnamyl
Pen(Mbzl) = S-(4-methylbenzyl)Penicillamine
Pep = 1-(2-Phenylethyl)piperazine
PFF = p-Fluorophenylalanine
βPhc = β-Phenylcinnamoyl
3Php = 3-Phosphonopropionyl
5Phv = 5-Phenylvaleroyl
Pic = Picolinoyl
PIF = p-Iodophenylalanine
Pipe = Piperidine
Pipp = 4-Piperidinopiperidine
Pipz = Piperazine
Piva = Pivaloyl (Trimethylacetyl)
Pmpz = 1-2-Pyrimidylpiperazine
PNF = p-Nitro-phenylalanine
Ppp = 1-(3-Phenylpropyl)piperazine
Ppr = Phenylpropiolyl
Ptmb = 4-(Trifluoromethyl)benzoyl
αPtpa = α-(Phenylthio)phenylacetyl
Pxa = Pyridoxamine [4-(aminomethyl)-5-hydroxy-
6-methyl-3-pyridinemethanol]
Pya = trans-3-(3-Pyridyl)acryloyl
Pypz = 1-2-Pyridylpiperazine
Pyrc = Pyridine-3-carboxyl
Pyz = Pyrazinoyl
3Qum = Quinoline-3-methyl
13cR = 13-cis-Retinoyl
Ret = trans-Retinoyl
Rio = Ricinoleyl TABLE 1-continued Abbreviations for Chemical Groups Used to Synthesize
the Anti-Cancer Compounds of the Present Invention Saa = trans-Styrylacetyl
Sab = 4-Surphamidobenzoyl
cSdc = cis-Stilbene-4,4'-dicarboxylic
Sibu = S-(+)-Ibuprofen
CSsa = cis-Styrenesulphonylacetyl
tBSts = trans-β-Styrenesulfonyl
Taa = 1,2,4-Triazole-acetyl
Tchc = (1R,3R,4S,5R)-1,3,4,5-Tetrahydrocyclohexane-
1-carboxyl
Tcpa = 2,4,5-Trichlorophenoxyacetyl
Tf2c = trans-3,5-bis(Trifluoromethyl)cinnamoyl
4Tfmb = 4-(Trifluoromethoxy)benzoyl
Thia = 3-(2-Thienyl)acryloyl
Th2n = 1,2,3,4-Tetrahydro-2-naphthoyl
Tic = Tetrahydroisoquinoline-3-carboxylic acid
Tmb = Trimethoxybenzoyl
Tmbp = 1-(2,4,6-Trimethylbenzyl)piperazine
4Tmbs = 4-(Trifluoromethoxy)benzenesulfonyl
Tmbz = Trimethoxybenzyl
Tmcc = 2,2,3,3-Tetramethylcyclopropanecarboxyl
Tmpc = Carboxy-TEMPO: 4-carboxy-2,2,6,6-
tetramethylpiperidinyloxy
Tyr(Bzl) = O-Benzyl-tyrosine
ZPcn = (Z)-α-Phenylcinnamoyl; (cis)

It will be appreciated by those skilled in the art that compounds of the invention having a chiral center may exist in, and be isolated in, optically active and racemic forms. Some compounds may exhibit polymorphism. It is to be understood that the present invention encompasses any racemic, optically-active, polymorphic, or stereoisomeric form, or mixtures thereof, of the anti-cancer compounds of the invention, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-cancer and anti-tumor activity using the in vitro and in vivo tests described herein, or using other similar tests which are well known in the art.

Prodrugs of the compounds of Formula I may be identified using routine techniques known in the art. Various forms of prodrugs are known in the art. For examples of such prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8, 1-38 (1992); d) H. Bundgaard, et al., Journal of Pharmaceutical Sciences, 77:285 (1988); and e) N. Kakeya, et al., Chem. Pharm. Bull., 32: 692 (1984), each of which is specifically incorporated herein by reference.

In addition, the invention also includes solvates, metabolites, and pharmaceutically acceptable salts of compounds of Formula I.

The term "solvate" refers to an aggregate of a molecule with one or more solvent molecules. A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

A "pharmaceutically acceptable salt" as used herein, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, .gamma.-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

In the embodiments of the present invention in which the anti-cancer compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

In the embodiments of the present invention in which the anti-cancer compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like. Other salts of acidic moieties may include, for example, those salts formed with procaine, quinine and N-methylglusoamine, plus salts formed with basic amino acids such as ornithine, histidine, lysine and arginine.

Whereas most of the results of in vivo anti-cancer activity of compounds reported in this application were obtained by intraperitoneal injection of compounds into nude mice bearing implanted tumors, reference compound M570 was shown to be active after oral administration.

The active anti-cancer compounds are effective over a wide dosage range and are generally administered in a therapeutically-effective amount. The dosage and manner of administration will be defined by the application of the anti-cancer agent and can be determined by routine methods of clinical testing to find the optimum dose. These doses are expected to be in the range of 0.001 mg/kg to 100 mg/kg of active compound. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

When employed as pharmaceuticals, the compounds of Formula I are administered in the form of pharmaceutical compositions. These compounds can be administered by a variety of routes including oral, rectal, transdermal, subcutaneous, intravenous, intramuscular, and intranasal. Preferably, the anti-cancer compounds of the present invention are administered via intratracheal instillation or aerosol inhalation when used to treat lung cancer. Such pharmaceutical compositions are prepared in a manner well known in the pharmaceutical art and comprise at least one active anti-cancer compound of Formula I.

The pharmaceutical compositions of the present invention contain, as the active ingredient, one or more of the compounds of Formula I above, associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of solutions, syrups, aerosols (as a solid or in a liquid medium), ointments containing, for example, up to 30% by weight of the active compound, soft and hard gelatin capsules, suppositories, sterile injectable solutions, and sterile packaged powders.

In preparing a formulation, it may be necessary to mill the anti-cancer compound to provide the appropriate particle size prior to combining with the other ingredients. If the anti-cancer compound is substantially insoluble, it ordinarily is milled to a particle size of less than 200 mesh. If the anti-cancer compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably these compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Additional objects, advantages, and novel features of this invention will become apparent to those skilled in the art upon examination of the following examples thereof, which are not intended to be limiting.

EXAMPLES

Example I

Synthesis of Compounds

Compounds were synthesized by standard organic chemistry procedures well known in the art. Compounds were purified by HPLC and were characterized by analytical HPLC, TLC, and LDMS. Examples of structures of compounds tested are given in Tables 2 and 3.

Example II

Synthesis of M570 Hydrochloride:
F5c-OC2Y-Atmp.HCl

4-Amino-2,2,6,6-tetramethylpiperidine (Aldrich) was coupled with Boc-(O-2,6-dichlorobenzyl)-tyrosine, using BOP in DMF solution. The Boc protecting group was removed by TFA and the product coupled with 2,3,4,5,6-pentafluorocinnamic acid in DMF, using BOP in the presence of excess DIEA at room temperature for 3 hours. The DMF was removed in vacuo, the product was extracted into ethyl acetate and the solvent was evaporated. The residue was treated with 0.1-1.0 N HCl or 20% ethanolic HCl. The solvent was removed by evaporation in vacuo at room temperature. The residue was lyophilized from water-dioxane or crystallized from ethanol-ether.

Example III

In Vitro Calorimetric Assay for Cell Survival

Cell growth and survival were measured by a rapid calorimetric assay based on the tetrazolium salt MTT (3-(4,5-dimethylthiazol-2-yl)-2,5-diphenyl tetrazolium bromide) (Mosmann, J. Immunol. Methods 65: 55-63, 1983, with minor modifications). Briefly, 1,000 normal lung fibroblasts or normal epithelial BEAS-2B cells, 1,000 or 5,000 viable non-SCLC cells or 10,000 viable SCLC cells were plated in 100 μL of growth medium in 96-well flat-bottomed microtiter plates. Cells were incubated overnight to allow recovery. Compounds to be tested were added to the cells in triplicate in a range of concentrations and the cells were incubated at 37° C., 5% $CO_2$, with 100% humidity. Control cells were treated in the same way without antagonists. All wells had a final volume of 200 μL. Plates were incubated for 4 days, allowing sufficient time for cell replication and compound-induced cell death to occur. On day 5, 25 μL of a 2 mg/mL solution of MTT (Sigma) dissolved in RMPI-1640 was added to each well. The plate was incubated for 4 h at 37° C. The supernatant liquid was removed and the blue formazan complex was dissolved by adding 100 μL of 0.02 N HCl in 75% isopropanol to all wells. Absorbance was immediately determined using a scanning multiwell plate reader. M570 caused 50% cell death at a concentration of 0.15 μM under these conditions. Examples of structures of compounds tested and their biological activities on cancers in vitro are given in Tables 2 and 3.

Example IV

Inhibition of Tumor Growth In Vivo in Nude Mice

Compounds having high in vitro cytotoxic activity were tested against implanted tumors in vivo. Athymic nude mice were implanted subcutaneously with suspensions (2 million SHP-77 SCLC cells, 1 million A549 NSCLC cells or 1.5 million PC3 PC cells) in Matrigel suspension. On the eighth day after tumor implantation groups of 5 mice bearing implants were injected intraperitoneally with the compounds being tested at 5 mg/kg/every second day or at 10 mg/kg/every fourth day; control animals were injected with an equal volume of isotonic saline. Less soluble compounds were initially dissolved in dimethyl sulfoxide (DMSO) and diluted with medium. In those cases the control injections contained the same concentration of DMSO. Tumor size was measured with a caliper three times per week. Tumor volume was calculated by the formula:

Volume(cc)=3.14×(length)×(width)$^2$/6

At autopsy tumors were removed and weighed. Tumor inhibition was calculated on both weight and measurement basis. Results of representative in vivo tests are given in Tables 2 and 3. In each Table, an IC50 value of "0" represents no detectable anti-cancer activity for a drug in a given cell line and "Stim." indicates the observation of a stimulatory activity on the growth of the cancer cell line. For comparison, reference compound M570 caused 85% inhibition of growth of the SCLC line SHP-77 and 65% inhibition of PC cell line PC3 tumors at a dose of 5 mg/kg/every second day or at 10 mg/kg/every fourth day.

TABLE 2

Structures and Activities of Anti-Cancer Compounds of the Present Invention

| Analog Number | Structure | SHP-77 In vitro IC$_{50}$, μM[a] | SHP-77 In vivo % inhib.[c] | A-549 In vivo % inhib.[c] | PC3 In vivo % inhib.[c] |
| --- | --- | --- | --- | --- | --- |
| M-1052 | F5c-Igl-Atmp | 7.3 | | | 27 |
| M-1054 | F5c-F5F-Atmp | 4.6 | | | 47 |
| M-1080 | F5c-OBPY-Atmp | 0 | | | |
| M-1092 | F5BS-OC2Y-Atmp | 14 | | | Stim. |
| M-1094 | F5PT-OC2Y-Atmp | 3.2 | | | 52 |
| M-1096 #1 | IMP-OC2Y-Atmp | 7.0 | | | |
| M-1096 #2 | IMP-OC2Y-Atmp | 4.0 | | | |
| M-1098 #1 | CHFB-OC2Y-Atmp | 0 | | | |
| M-1098 #2 | CHFB-OC2Y-Atmp | 6.8 | | | |
| M-1100 | Gun-Cys-OC2Y-Matp | 13 | | | 13 |
| M-1108 | F5c-D-OC2Y-Atmp | 0 | | | 46 |
| M-1110 | F5c-PCNF-Atmp | 0.9 | | | 54 |
| M-1112 | F5c-PNF-Atmp | 30 | | | 24 |
| M-1114 | F5c-Trp-Atmp | 0 | | | 28 |
| M-1116 | Dca-OC2Y-Atmp | 7.5 | | | 19 |
| M-1118 | F5c-OC2Y-Atmp(2Me) | 1.8 | | | |
| M-1120 | Glu-Trp-Atmp | 0 | | | |
| M-1124#1 | Chpa-OC2Y-Atmp | 1.7 | | 50 | Stim |
| M-1124#2 | Chpa-OC2Y-Atmp | 3.5 | | 4.5 | |
| M-1126 | 22Dp-OC2Y-Atmp | 4.0 | | 36 | |
| M-1128 | Rio-OC2Y-Atmp | 1.6 | | 48 | 44 |
| M-1140 | F5c-PFF-Atmp | 15 | | | |
| M-1142 | F5c-PIF-Atmp | 7.2 | | | |
| M-1144 | F5c-PBF-Atmp | 7.2 | | | 20 |
| M-1146 | F5c-F3MF-Atmp | 12 | | | |
| M-1148 | F5c-NMF-Atmp | 15.5 | | | |
| M-1150 | F5c-Dip-Atmp | 5 | | | |
| M-1152 | 3-Fa-PFF-Atmp | 0 | | | |
| M-1154 | 2-Fa-PFF-Atmp | 0 | | | Stim |
| M-1156 | F5c-PFF-Abzp | 7.5 | | | 56 |
| M-1158 | F5c-PFF-Mpz | 28 | | | |
| M-1160 | F5c-PFF-Dmpz | 24 | | | |
| M-1162 | F5c-PFF-Pmpz | 15 | | | |
| M-1164 | F5c-PFF-Pypz | 14 | | | |
| M-1174 | F5c-Bip-Atmp | 3.7 | | 57 | 37 |
| M-1176 | F5c-hPhe-Atmp | 14 | | | |
| M-1178 | F5c-Phe-Atmp | 15 | | | |
| M-1180 | F5c-PIF-Abzp | 3.2 | | 23 | 53 |
| M-1182 | F5c-F5F-Abzp | 19.5 | | | |
| M-1186 | F5c-F5F-Dmpz | 11 | | | |
| M-1188 | Bcpa-F5F-Abzp | 4.5 | | 17 | |
| M-1200 | F5c-Nal-Dpic | 5.0 | | Stim | |
| M-1202 | F5c-PFF-Cbp | 30 | | | |
| M-1204 | Pya-Nal-Cbp | 7.5 | | | |
| M-1208 | F5c-PFF-Cpp | 30 | | | |
| M-1212 | Pya-PFF-Cpp | 10 | | | |
| M-1214 | Bcpa-Nal-Dpic | 7.3 | | 24 | 37 |
| M-1216 | F5c-Nal-Pypz | 0 | | 32 | 22 |
| M-1218 | F5c-Aic-Dpic | 14 | | | |
| M-1242 | Bcpa-Nal-Pypz | 0 | | 19 | 36 |
| M-1244 | Bcpa-Bip-Atmp | 1.3 | | | 59 |
| M-1246 | Bcpa-Nal-Pipp | 3.6 | | | Stim |
| M-1248 | F5c-PIF-Pypz | 13 | | | |
| M-1250 | F5c-Nal-Pipp | 7.6 | | | |
| M-1252 | Tf2c-PIF-Pypz | 0 | | | |
| M-1254 | F5c-PIF-Dmpz | 10 | | | |
| M-1256 | F5c-PIF-Dpic | 13 | | | |
| M-1258 | F5c-Bip-Pypz | 48 | | | 10 |
| M-1260 | F5c-Bip-Pmpz | 10 | | | 60 |
| M-1268 | F5c-Bip-Bdbh | 3 | | | 36 |

TABLE 3

Structures and Activities of Anti-Cancer Compounds of the Present Invention

| Analog Number | Structure | NSCLC A-549 IC$_{50}$, μM[b] | SCLC SHP-77 IC$_{50}$, μM[a] | SHP-77 In vivo % inhib.[c] | A-549 In vivo % inhib.[c] | PC3 In vivo % inhib.[c] |
|---|---|---|---|---|---|---|
| M-1272 | F5c-Bip-Fpdh | 22 | 10 | | | 71 |
| M-1274 | Bcpa-Bip-Atmp | 7.3 | 2.1 | | | |
| M-1276 | Bcpa-Bip-Bdbh | 20 | 0 | | | 56 |
| M-1278 | F5c-Bip-Aqu | | | | | |
| M-1280 | F5c-PIF-Bdbh | 20 | 10 | | | 40 |
| M-1284 | F5c-PIF-Dasd | 20 | 22 | | | Stim. |
| M-1286 | F5c-PIF-(R)-(+)-Aqu | 9.0 | 4.3 | | | |
| M-1288 | F5c-Bip-(R)-(+)-Aqu | 7.3 | 4.3 | | | |
| M-1290 | F5c-PIF-(S)-(−)-Aqu | 14 | | | | |
| M-1292 | F5c-Bip-(S)-(−)-Aqu | 9.8 | | | | |
| M-1294 | F5c-PIF-Bhp | 22 | | | | 44 |
| M-1296 | F5c-Bip-Bhp | | | | | |
| M-1298 | F5c-PIF-Cpp | 21 | | | | |
| M-1300 | F5c-PIF-Cbp | 21 | | | | |
| M-1304 | F5c-PIF-Pep | 17 | | | | |
| M-1306 | F5c-PIF-3-Abzp | 18 | | | | |
| M-1308 | F5c-PIF-Ppp | 14 | | | | |
| M-1310 | F5c-PIF-4-Clbp | 12 | | | | Stim. |
| M-1312 | F5c-PIF-BapS | 13 | | | | 33 |
| M-1314 | F5c-PIF-Chmp | 21 | | | | |
| M-1316 | F5c-PIF-Alp | 20 | | | | |
| M-1318 | F5c-PIF-Daep | 8.4 | | | | |
| M-1320 | F5c-PIF-4-Cypp | 17 | | | | |
| M-1322 | F5c-PIF-Fbp | 13 | | | | 46 |
| M-1324 | F5c-PIF-Chep | 15 | | | | 44 |
| M-1326 | F5c-PIF-BapR | 10 | | | | 0.6 |
| M-1328 | F5c-PIF-2-Cypp | 14 | | | | |
| M-1330 | F5c-PIF-Ocp | 17 | | | | 40 |
| M-1332 | F5c-PIF-4-Mbp | 7.8 | | | | 63 |
| M-1334 | F5c-PIF-Tmbp | 19 | | | | 50 |
| M-1336 | F5c-PIF-Fpmp | 12 | | | | 71 |
| M-1342 | F5c-PIF-Fbhp | | | | | |
| M-1350 | Pic-OC2Y-Atmp | | 6.1 | | 36 | |
| M-1352 | Pic-PCNF-Atmp | | 0 | | 21 | |
| M-1354 | Pic-Igl-Atmp | | 0 | | | |
| M-1356 | F5pa-OC2Y-Atmp | | 4.4 | | 0 | |
| M-1358 | F5po-OC2Y-Atmp | | 4.1 | | | 30 |
| M-1360 | F5bz-OC2Y-Atmp | | 4.1 | | | Stim. |
| M-1362 | 3,4Dmc-OC2Y-Atmp | | 4.0 | | 21 | |
| M-1364 | 3Ibu-OC2Y-Atmp | | 7.2 | | 50 | 9 |
| M-1366 | Dmo-OC2Y-Atmp | | 3.8 | | 14 | |
| M-1368 | 2Pyz-OC2Y-Atmp | | 3.2 | | 47 | Stim. |
| M-1372 | Bbz-OC2Y-Atmp | | 0 | | 64 | |
| M-1374 | Bbz-Igl-Atmp | | 0 | | | |
| M-1376 | Indo-OC2Y-Atmp | 1.8 | 1.5 | | 18 | 44 |
| M-1378 | Aspr-OC2Y-Atmp | 3.5 | 2.9 | | 9 | Stim. |
| M-1380 | Napr-OC2Y-Atmp | 1.6 | 1.7 | | | 26 |
| M-1382 | Dfc-OC2Y-Atmp | | 2.9 | | 46 | |
| M-1384 | Chl-OC2Y-Atmp | 1.9 | 1.8 | | 46 | Stim. |
| M-1386 | Tmpc-OC2Y-Atmp | | 12 | | | 20 |
| M-1388 | F3c-OC2Y-Atmp | | 1.6 | | 21 | Stim. |
| M-1390 | Gbz-OC2Y-Atmp | 4.3 | >40 | | | Stim. |
| M-1392 | Ktpf-OC2Y-Atmp | | 2.9 | | 28 | 18 |
| M-1394 | Ktlc-OC2Y-Atmp | 4.9 | 2.9 | | 68 | Stim. |
| M-1396 | Dhq-OC2Y-Atmp | | 15 | | | 9 |
| M-1398 | Ppr-OC2Y-Atmp | | 8.0 | | | 65 |
| M-1400 | Pcn-OC2Y-Atmp | | 1.3 | | | Stim. |
| M-1402 | Hcn-OC2Y-Atmp | | 0 | | | Stim. |
| M-1406 | Tmcc-OC2Y-Atmp | | 5.3 | | | 25 |
| M-1408 | 3,4,5Tmb-OC2Y-Atmp | | 8.0 | | | Stim. |
| M-1412 | 2Octe-OC2Y-Atmp | | 12 | | | 38 |
| M-1414 | 34Mdc-OC2Y-Atmp | | 7.1 | | | Stim. |
| M-1416 | Tchc-OC2Y-Atmp | | 0 | | | 0 |
| M-1418 | Thia-OC2Y-Atmp | | 8.6 | | | 9 |
| M-1420 | Atfb-OC2Y-Atmp | | 12 | | | Stim. |
| M-1422 | Cpcpc-OC2Y-Atmp | | 13 | | | 31 |
| M-1430 | F5c-Pen(Mbzl)-Atmp | | 6.1 | | | 50 |
| M-1432 | F5c-PFF-Dmmp | | 18 | | | |
| M-1434 | 3Pal-OC2Y-Atmp | | 3.8 | Stim. | | |
| M-1436 | Biot-OC2Y-Atmp | | 0 | | | |
| M-1440 | Th2n-OC2Y-Atmp | | 3.5 | | | 15 |
| M-1442 | Arac-OC2Y-Atmp | | 6.4 | | | 31 |
| M-1444 | Tf2c-OC2Y-Atmp | | 1.4 | | | 11 |

TABLE 3-continued

Structures and Activities of Anti-Cancer Compounds of the Present Invention

| Analog Number | Structure | NSCLC A-549 IC$_{50}$, μM$^b$ | SCLC SHP-77 IC$_{50}$, μM$^a$ | SHP-77 In vivo % inhib.$^c$ | A-549 In vivo % inhib.$^c$ | PC3 In vivo % inhib.$^c$ |
|---|---|---|---|---|---|---|
| M-1446 | Ret-OC2Y-Atmp | | 6.7 | | | 60 |
| M-1448 | 2Ina-OC2Y-Atmp | | 13 | | | 11 |
| M-1450 | 2Hyb-OC2Y-Atmp | | 13 | | | Stim. |
| M-1452 | Atfb-OC2Y-Atmp | | 7.2 | | | Stim. |
| M-1456 | Fcin-OC2Y-Atmp | | 4.0 | | | 17 |
| M-1458 | Sab-OC2Y-Atmp | | 0 | | | Stim. |
| M-1460 | Bcin-OC2Y-Atmp | | 23 | | | 38 |
| M-1462 | Hor-OC2Y-Atmp | | 0 | | | 7 |
| M-1464 | Aba-OC2Y-Atmp | | 14 | | | 14 |
| M-1466 | Biot-PCNF-Atmp | | 0 | | | 29 |
| M-1468 | Biot-Pen(Mbzl)-Atmp | | 0 | | | 46 |
| M-1470 | Ret-Pen(Mbzl)-Atmp | | | | | |
| M-1472 | Ret-PCNF-Atmp | | | | | |
| M-1474 | 3Ibu-Pen(Mbzl)-Atmp | | 7.8 | | | Stim. |
| M-1476 | 3Ibu-PCNF-Atmp | | 0 | | | |
| M-1478 | Rio-PCNF-Atmp | | 14 | | | |
| M-1480 | Tmpc-Pen(Mbzl)-Atmp | | 0 | | | Stim. |
| M-1482 | Tmpc-PCNF-Atmp | | 0 | | | |
| M-1484 | Ptmb-OC2Y-Atmp | | 1.8 | | | Stim. |
| M-1486 | F5po-Pen(Mbzl)-Atmp | | 4.2 | | | 21 |
| M-1488 | F5po-PCNF-Atmp | | 0 | | | |
| M-1490 | F5bz-PCNF-Atmp | | >60 | | | |
| M-1492 | Aca-Pen(Mbzl)-Atmp | | 3.4 | | | 15 |
| M-1494 | Aca-OC2Y-Atmp | | 1.6 | | | 40 |
| M-1496 | Aca-PCNF-Atmp | | >60 | | | 2 |
| M-1498 | Chl-Pen(Mbzl)-Atmp | | 3.5 | | | 20 |
| M-1500 | Chl-PCNF-Atmp | | 25 | | | |
| M-1502 | F3c-Pen(Mbzl)-Atmp | | 3.4 | | | 11 |
| M-1504 | F3c-PCNF-Atmp | | >60 | | | |
| M-1506 | Napr-Pen(Mbzl)-Atmp | | 4.7 | | | 13 |
| M-1508 | Napr-PCNF-Atmp | | 23 | | | 45 |
| M-1510 | 22Dp-Pen(Mbzl)-Atmp | | 4.2 | | | Stim. |
| M-1512 | 22Dp-PCNF-Atmp | | 22 | | | 48 |
| M-1514 | Dca-Pen(Mbzl)-Atmp | | 7.3 | | | |
| M-1516 | Dca-PCNF-Atmp | | 11 | | | |
| M-1518 | Indo-Pen(Mbzl)-Atmp | | 6.0 | | | Stim. |
| M-1520 | Indo-PCNF-Atmp | | 13 | | | Stim. |
| M-1522 | 2Pyz-Pen(Mbzl)-Atmp | | 31 | | | Stim. |
| M-1524 | 2Pyz-PCNF-Atmp | | >60 | | | |
| M-1528 | Fmpi-OC2Y-Atmp | | 1.7 | | | |
| M-1532 | Esul-OC2Y-Atmp | 5 | 4.0 | | 54 | 42 |
| M-1536 | 4Tmbs-OC2Y-Atmp | | 3.2 | | | Stim. |
| M-1538 | 4Tfmb-OC2Y-Atmp | | 1.8 | | | Stim. |
| M-1542 | 4Bpc-OC2Y-Atmp | | 6.4 | | | Stim. |
| M-1544 | F5c-OC2Y-(R)-Aqu | | 6.0 | | | 28 |
| M-1546 | F5c-OC2Y-(S)-Aqu | | 1.8 | | | 29 |
| M-1548 #1 | Chpa-OC2Y-(R)-Aqu | | 4.0 | | | |
| M-1548 #2 | Chpa-OC2Y-(R)-Aqu | | 13 | | | |
| M-1550 #1 | Chpa-OC2Y-(S)-Aqu | | 2.5 | | | 36 |
| M-1550 #2 | Chpa-OC2Y-(S)-Aqu | | 4.0 | | | Stim. |
| M-1552 | F5c-OC2Y-Abzp | | 13 | | | 52 |
| M-1554 | F5c-OC2Y-Pmpz | | 6.8 | | | Stim. |
| M-1556 | F5c-OC2Y-cDmbp | | 18 | | | 59 |
| M-1558 | Indo-OC2Y-Abzp | | 9.6 | | | Stim. |
| M-1560 | Indo-OC2Y-cDmbp | | 0 | | | Stim. |
| M-1562 | Indo-OC2Y-Pmpz | | 0 | | | 2 |
| M-1564 | F5c-OC2Y-tCip | | 4.0 | | | |
| M-1566 | Indo-OC2Y-tCip | | 0 | | | 57 |
| M-1568 | Cmioc-OC2Y-Atmp | | 3.6 | | | Stim. |
| M-1574 | Dbhc-OC2Y-Atmp | | 1.6 | | | Stim. |
| M-1576 | Bzac-OC2Y-Atmp | | 6.2 | | | 57 |
| M-1578 | F5c-OC2Y-Dcpp | | | | | Stim. |
| M-1580 | Indo-OC2Y-Dcpp | | | | | |
| M-1582 | F5c-OC2Y-Amp | | 6.7 | | | 60 |
| M-1584 | Indo-OC2Y-Amp | | 1.5 | | | 32 |
| M-1586 | Indo-D-OC2Y-Atmp | | 1.7 | | | 38 |
| M-1588 | Indo-OC2Y-(R)-Aqu | | 3.9 | | | 8 |
| M-1590 | Indo-OC2Y-(S)-Aqu | | 4.1 | | | Stim. |
| M-1592 | Pas-OC2Y-Atmp | | 7.2 | | | Stim. |
| M-1594 | F5b-OC2Y-Atmp | | 3.1 | | | 20 |
| M-1596 | 6Ani-OC2Y-Atmp | | 0 | | | |
| M-1598 | fDecl-OC2Y-Atmp | | 4.1 | | | |
| M-1600 | Pcnl-OC2Y-Atmp | | 4.1 | | | 44 |

TABLE 3-continued

Structures and Activities of Anti-Cancer Compounds of the Present Invention

| Analog Number | Structure | NSCLC A-549 IC$_{50}$, μM[b] | SCLC SHP-77 IC$_{50}$, μM[a] | SHP-77 In vivo % inhib.[c] | A-549 In vivo % inhib.[c] | PC3 In vivo % inhib.[c] |
|---|---|---|---|---|---|---|
| M-1602 | Acrc-OC2Y-Atmp | | 1.6 | | | Stim. |
| M-1604 | 3Qum-OC2Y-Atmp | | 7.4 | | | Stim. |
| M-1606 | F5c-OC2Y-Bhp | | 17 | | | |
| M-1608 | F5c-ObrZY-Atmp | | 10 | | | 29 |
| M-1610 | B6-OC2Y-Atmp | | 0 | | | Stim. |
| M-1612 | B6P-OC2Y-Atmp | | 0 | | | Stim. |
| M-1614 | F5c-OC2Y-cDmap | | 2.0 | | | 54 |
| M-1616 | 3Php-OC2Y-Atmp | | 0 | | | 18 |
| M-1618 | Aq2c-OC2Y-Atmp | | 2.2 | | | 10 |
| M-1622 | F5c-OC2Y-Pxa | | 22 | | | 58 |
| M-1624 | F5c-OC2Y-Ambi | | 50 | | | 68 |
| M-1628 | Amts-OC2Y-Atmp | | 45 | | | |
| M-1630 | Otac-OC2Y-Atmp | | 60 | | | 71 |
| M-1632 | F5c-OC2Y-Aem | | 7.8 | | | 32 |
| M-1634 | F5b-OC2Y-tCip | | 0 | | | Stim. |
| M-1636 | F5c-OC2Y-Pipz | | | | | |
| M-1638 | Chc-OC2Y-Atmp | | 18 | | | 39 |
| M-1642 | F5c-OC2Y-Apia | | 42 | | | |
| M-1648 | Pac-OC2Y-Atmp | | 7.6 | | | 28 |
| M-1650 | Nba-OC2Y-Atmp | | 4.3 | | | 40 |
| M-1652 | 2Ccn-OC2Y-Atmp | | 4.1 | | | |
| M-1654 | Pcn-OC2Y-tCip | | 0 | | | |
| M-1656 | Biot-OC2Y-tCip | | 5.5 | | | |
| M-1658 | Pcn-OC2Y-Amp | | 10 | | | |
| M-1660 | Pcn-OC2Y-Abzp | | 31 | | | |
| M-1662 | Pcn-OC2Y-cDmbp | | 20 | | | |
| M-1664 | Ktlc-OC2Y-cDmbp | | 0 | | | |
| M-1666 | Ktlc-OC2Y-tCip | | 0 | | | |
| M-1668 | Ktlc-OC2Y-Abzp | | 4.6 | | | |
| M-1670 | Pcn-OC2Y-Pmpz | | 50 | | | |
| M-1672 | Aaa-OC2Y-Pmpz | | >50 | | | |
| M-1674 | Ktlc-OC2Y-Amp | | 3.2 | | | |
| M-1676 | Aca-OC2Y-Amp | | 6.2 | | | |
| M-1678 | Aca-OC2Y-Abzp | | 7.8 | | | |
| M-1680 | Aca-OC2Y-Pmpz | | 33. | | | |
| M-1682 | Pcn-D-OC2Y-Atmp | | 1.8 | | | |
| M-1684 | Pcn-Igl-Atmp | | 4.2 | | | |
| M-1686 | Ktlc-Igl-Atmp | | 14 | | | |
| M-1688 | Indo-Igl-Atmp | | 4.0 | | | |
| M-1690 | F5c-Igl-Pipz(F5b) | | 25 | | | |
| M-1692 | Dcla-OC2Y-Atmp | | 7.2 | | | |
| M-1698 | Dbhc-OC2Y-Amp | | 4.2 | | | |
| M-1700 | Acrc-OC2Y-Amp | | 7.3 | | | |
| M-1702 | Aq2c-OC2Y-Amp | | 3.6 | | | |
| M-1704 | Pyrc-OC2Y-Atmp | | 25 | | | |
| M-1706 | 1Nap-OC2Y-Atmp | | 4.2 | | | |
| M-1708 | 1Nala-OC2Y-Atmp | | 7.2 | | | |
| M-1710 | 2Nala-OC2Y-Atmp | | 1.7 | | | |
| M-1712 | 5Phv-OC2Y-Atmp | | | | | |
| M-1714 | 2Cln-OC2Y-Atmp | | 4.0 | | | |
| M-1716 | Hmqc-OC2Y-Atmp | | 7.2 | | | |
| M-1718 | Baaa-OC2Y-Atmp | | 0 | | | |
| M-1720 | Tcpa-OC2Y-Atmp | | | | | |
| M-1722 | F5c-OC2Y-Pipe(Btmb) | | 26 | | | |
| M-1724 | Pcn-OC2Y-Pipe(Btmb) | | 0 | | | |
| M-1726 | F5c-OC2Y-Pipz(Tmbz) | | 26 | | | |
| M-1728 | Pcn-OC2Y-Pipz(Tmbz) | | 26 | | | |
| M-1730 | F5c-F5F-Pipz(F5b) | | 21 | | | |
| M-1732 | F5c-OC2Y-Pipz(F5b) | | 24 | | | |
| M-1734 | Pcn-OC2Y-Pipz(F5b) | | 24 | | | |
| M-1736 | Piva-OC2Y-Atmp | | 13 | | | |
| M-1738 | F5c-OC2Y-Apyr(Tmbz) | | 24 | | | |
| M-1742 | Otac-OC2Y-Ambi | | | | | |
| M-1744 | Mcoa-OC2Y-Atmp | | 7.1 | | | |
| M-1746 | Chbu-OC2Y-Atmp | | 1.6 | | | |
| M-1748 | tBua-OC2Y-Atmp | | 7.1 | | | |
| M-1750 | (S)-MTPA-OC2Y-Atmp | | 4.2 | | | |
| M-1752 | (R)-MTPA-OC2Y-Atmp | | 4.0 | | | |
| M-1754 | Bcpa-OC2Y-Atmp | | 1.5 | | | |
| M-1756 | Bcpoa-OC2Y-Atmp | | | | | |
| M-1758 | αMcn-OC2Y-Atmp | | | | | |
| M-1760 | Pcn-OCIY-Atmp | | 2.0 | | | |
| M-1762 | Bcpa-OCIY-Atmp | | 3.0 | | | |

TABLE 3-continued

Structures and Activities of Anti-Cancer Compounds of the Present Invention

| Analog Number | Structure | NSCLC A-549 IC$_{50}$, μM[b] | SCLC SHP-77 IC$_{50}$, μM[a] | SHP-77 In vivo % inhib.[c] | A-549 In vivo % inhib.[c] | PC3 In vivo % inhib.[c] |
|---|---|---|---|---|---|---|
| M-1764 | Pcn-Bip-Atmp | | 2.5 | | | |
| M-1766 | Bcpoa-Bip-Atmp | | 2.0 | | | |
| M-1770 | Pcn-Tic-Atmp | | 5.4 | | | |
| M-1772 | Pcn-Tyr(Bzl)-Atmp | | | | | |
| M-1774 | 13cR-OC2Y-Atmp | | | | | |
| M-1776 | Pcin-OC2Y-Atmp | | 1.4 | | | |
| M-1778 | Mca-OC2Y-Atmp | | 1.5 | | | |
| M-1780 | Saa-OC2Y-Atmp | | 1.8 | | | |
| M-1782 | Bipa-OC2Y-Atmp | | 3.0 | | | |
| M-1786 | Taa-OC2Y-Atmp | | 0 | | | |
| M-1788 | Pcn-PFF-Atmp | | 2.3 | | | |
| M-1790 | Pcn-F3MF-Atmp | | 2.2 | | | |
| M-1796 | Bipa-Bip-Atmp | | 1.5 | | | |
| M-1798 | Fmoc-Leu-Atmp | | 7.6 | | | |
| M-1800 | Fmoc-OC2Y-Atmp | | 1.7 | | | |
| M-1804 | Pcn-MC2Y-Atmp | | | | | |
| M-1806 | αPtpa-OC2Y-Atmp | | | | | |
| M-1808 | cSsa-OC2Y-Atmp | | | | | |
| M-1810 | 1Nac-OC2Y-Atmp | | | | | |
| M-1812 | cSdc-OC2Y-Atmp | | | | | |
| M-1816 | Bcpa-Dip-Atmp | | | | | |
| M-1832 | 3Iac-Bip-Atmp | | | | | |
| M-1834 | F5c-OC2Y-AtmpO | | | | | |
| M-1836 | ZPcn-OC2Y-Atmp | | | | | |
| M-1838 | tβSts-OC2Y-Atmp | | | | | |
| M-1840 | βPhc-OC2Y-Atmp | | | | | |
| M-1842 | αFcn-OC2Y-Atmp | | | | | |
| M-1844 | Nif-OC2Y-Atmp | | | | | |
| M-1846 | Nif-Bip-Atmp | | | | | |
| M-1848 | SIbu-OC2Y-Atmp | | | | | |
| M-1850 | SIbu-Bip-Atmp | | | | | |
| M-1852 | Fmoc-Bip-Atmp | | | | | |
| M-1854 | Bphs-OC2Y-Atmp | | | | | |
| M-1856 | Bphs-Bip-Atmp | | | | | |
| M-1858 | αFcn-Bip-Atmp | | | | | |
| M-1862 | 2Nac-OC2Y-Atmp | | | | | |
| M-1864 | Bipa-F3MF-Atmp | | | | | |
| M-1868 | Pcn-PIF-Atmp | | | | | |

Footnotes:
[a]ED$_{50}$ for killing of SCLC strain SHP-77 in vitro, μM.
[b]ED$_{50}$ for killing of NSCLC strain A-549 in vitro, μM.
[c]Percent inhibition of tumor growth in vivo in nude mice. PC3 is prostate cancer.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. An anti-cancer compound having the chemical composition:

X—O-2,6-dichlorobenzyl tyrosine-4-Amino-2,2,6,6-tetramethylpiperidine, wherein X is a chemical group selected from the group consisting of:

α-Phenylcinnamoyl-;
1-[p-Chlorobenzoyl]-5-methoxy-2-methylindole-3acetyl- (Indomethacin);
6-Methoxy-α-methyl-2-Naphthaleneacetyl- (Naproxen);
4-[p-(bis[2-Chloroethyl]amino)-phenyl]butyryl- (Chlorambucil);
2,3,5-Trifluorocinnamoyl-;
1-Adamantanecarboxyl-;
bis(4-Chlorophenyl)acetyl-; and,
2-Methylcinnamoyl-.

2. The anti-cancer compound of claim 1, wherein the O-2,6-dichlorobenzyl tyrosine moiety is the D-isomer (D-O-2,6-dichlorobenzyl tyrosine).

3. A prodrug of the anti-cancer compound of claim 1.

4. A pharmaceutically-acceptable salt of the anti-cancer compound of claim 1.

5. A pharmaceutical composition comprising an anti-cancer compound of claim 1 and at least one of an excipient and a pharmaceutically-acceptable carrier.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Arg Pro Pro Gly Phe Ser Pro Phe Arg
1               5
```